US008865235B2

(12) United States Patent
Diehl et al.

(10) Patent No.: US 8,865,235 B2
(45) Date of Patent: Oct. 21, 2014

(54) MICROBICIDAL AND ANTIPARASITIC COMPOSITIONS

(71) Applicant: Life Science Investments Limited, Kent (GB)

(72) Inventors: Christian Diehl, B Lomas de San Martin (AR); Silvia Chami De Diehl, B Lomas de San Martin (AR)

(73) Assignee: Life Science Investments, Ltd., Kent (GB)

( * ) Notice: Subject to any disclaimer, the term of this patent is extended or adjusted under 35 U.S.C. 154(b) by 0 days.

(21) Appl. No.: 14/013,633

(22) Filed: Aug. 29, 2013

(65) Prior Publication Data

US 2014/0005259 A1    Jan. 2, 2014

Related U.S. Application Data

(62) Division of application No. 11/659,713, filed as application No. PCT/IB2004/001865 on Mar. 12, 2004, now Pat. No. 8,568,794.

(51) Int. Cl.
| | |
|---|---|
| *A01N 65/00* | (2009.01) |
| *A61K 31/352* | (2006.01) |
| *A61K 31/366* | (2006.01) |
| *A61K 9/00* | (2006.01) |
| *A61K 9/02* | (2006.01) |
| *A61K 31/365* | (2006.01) |
| *A61K 36/185* | (2006.01) |

(52) U.S. Cl.
CPC ............. *A61K 31/352* (2013.01); *A01N 65/00* (2013.01); *A61K 9/0014* (2013.01); *A61K 9/0034* (2013.01); *A61K 9/02* (2013.01); *A61K 31/365* (2013.01); *A61K 31/366* (2013.01); *A61K 36/185* (2013.01)
USPC ......................................... 424/725; 514/453

(58) Field of Classification Search
CPC .... A61K 31/352; A61K 31/366; A01N 65/00
See application file for complete search history.

(56) References Cited

U.S. PATENT DOCUMENTS

| | | | |
|---|---|---|---|
| 5,676,948 A | 10/1997 | Bonte et al. | |
| 5,965,493 A | 10/1999 | Grieco et al. | |

FOREIGN PATENT DOCUMENTS

| | | |
|---|---|---|
| CN | A-1438016 | 8/2003 |
| KR | A-2002-0062474 | 7/2002 |
| KR | A-2003-0023913 | 3/2003 |

OTHER PUBLICATIONS

M. Onanga et al., "Ethnobotanical, Pharmacological and Chemical Studies of Plants Used in the Treatment of 'Mwandza' Dermatites", Fitoterapia, vol. 70, No. 6, (1999) pp. 579-585.
S. Loayza et al., "Antibacterial Activities of Medicinal Plants of the Ucayali (Peruvian Amazon)", Plantes Medicinales Et Phytotherapie, vol. 22, No. 4, (1988) pp. 254-260.
"WHO Monographs on Selected Medicinal Plants", World Health Organization, vol. 1, URL:http://www.who.int/medicines/library/trm/medicinalplants/pdf/059to066.pdf> (1999) pp. 59-66.
J. Polonsky, "Chemistry and Biological Activity of the Quassinoids", Chemistry and Chemical Taxonomy of the Rutales, Chapter 8, (1983) pp. 247-266.
M. Okano et al., "Biologically Active Compounds from Simaroubaceous Plants", Studies in Natural Products Chemistry, vol. 7 (1990) pp. 369-404.
G. Vitányi et al., "Application of High Performance Liquid Chromatography/Mass Spectrometry with Thermospray Ionization to the Detection of Quassinoids Extracted from *Quassia amara* L", Rapid Communications in Mass Spectrometry, vol. 11, (1997) pp. 691-693.
J. Dou et al., "Qualitative and Quantitative High Performance Liquid Chromatographic Analysis of Quassinoids in Simaroubaceae Plants", Phytochemical Analysis, vol. 7, (1996) pp. 192-200.
F. E. Dayan et al., "Phytotoxicity of Quassinoids: Physiological Responses and Structural Requirements", Pesticide Biochemistry and Physiology, vol. 65, (1999) pp. 15-24.
S. M. Simão et al., "Chemogeographical Evolution of Quassinoids in Simaroubaceae", Phytochemistry, vol. 30, No. 3, (1991) pp. 853-865.
E. S. Fernando et al., "*Picramniaceae*, A New Family, and a Recircumscription of Simaroubaceae", Taxon 44, (May 1995) pp. 177-181.
Z. Guo et al., "Biologically Active Quassinoids and Their Chemistry: Potential Leads for Drug Design," Current Medicinal Chemistry, vol. 12, pp. 173-190, 2005.
J. Polonsky et al., "Activity of Quassinoids as Antifeedants Against Aphids," Journal of Chemical Ecology, vol. 15, No. 3, pp. 993-998, 1989.
The European Agency for the Evaluation of Medicinal Products, Aug. 1999.

*Primary Examiner* — Bong-Sook Baek
(74) *Attorney, Agent, or Firm* — Oliff PLC

(57) ABSTRACT

Pharmaceutical or dermo-dermo-cosmetic compositions for topical and intravaginal application for treatment of human and veterinary affections caused by anaerobic organisms or parasites comprising quassinoids or plant extracts containing these phytochemicals, in effective amounts. Such compositions can be administered topically or intravaginally to patients in need thereof in various pharmaceutical dosage forms.

8 Claims, No Drawings

MICROBICIDAL AND ANTIPARASITIC COMPOSITIONS

This is a Division of application Ser. No. 11/659,713 filed Apr. 28, 2007, which in turn is a U.S. national stage application of International Application No. PCT/IB2004/001865 filed Mar. 12, 2004. The disclosure of the prior applications is hereby incorporated by reference herein in its entirety.

The present invention relates to pharmaceutical or dermocosmetic formulations for topical and intravaginal application, suitable for the treatment of various topical and vaginal infections, as well in humans as in veterinary medicine.

The present compositions comprise of one or more quassinoids, or plant extracts containing these phytochemicals, and have a wide spectra of activities, especially for the treatment of skin or mucosal disorders in which parasites and anaerobic bacteria might play a role as a cause or as a cofactor. Such skin or mucosal disorders, human and animal, include:

Facial erythrosis, couperose, rosacea.
Seborrheic dermatitis
Anaerobic infections of the skin
Leishmaniasis
Scabies (human and veterinary)
Trichomoniasis
Vaginitis with *Gardnerella*
Scabies
Demodectic mange (veterinary)

Facial Erythrosis, Couperose, and Rosacea

Rosacea is well recognized as a chronic cutaneous disorder primarily of the convexities of the central face (cheeks, chin, nose and central forehead) often characterized by remissions and exacerbations. Based on the present knowledge, it is considered a syndrome, or typology, encompassing various combinations of such cutaneous signs as flushing, erythema, telangiectasia, edema, papules, pustules, ocular lesions and rhinophyma. In most cases, some rather than all of these stigmata appear in any given patient.

Rosacea appears to be quite common, and has been most frequently observed in patients with fair skin. Rosacea occurs in both men and women and, although it may occur at any age, the onset typically begins at any time after age 30. Despite its apparent high incidence, the nosology of rosacea is not well established, and its etiology and pathogenesis are unknown, as there are no histological nor serologic markers.

The presence of one or more of the following signs with a central face distribution is indicative of rosacea: flushing, non-transient erythema, papules, pustules or telangiectasia. Other signs or symptoms often appear: burning or stinging sensations, elevated red plaques, roughness and scaly appearance of central facial skin, edema, and ocular manifestations ranging from symptoms of burning and itching to signs of conjunctival hyperemia and lid inflammations.

Pathogenesis of rosacea is currently not well understood, and it appears to be essentially a cutaneous vascular disorder: the first definition grade of rosacea is vascular, and no microorganisms were identified at this stage. Nonetheless, the role of *Demodex folliculorum* in the pathogenesis of rosacea was under discussion and investigated for a long time. Several clinical studies demonstrated that *Demodex folliculorum* was present in a huge majority of patients affected by rosacea, whilst it was present in a few unaffected ones. Then, it is currently accepted that *Demodex folliculorum* might represent at least an important cofactor in rosacea, especially in papulopustular rosacea. This parasite might play a role in the inflammatory reaction of the disease. It was also suggested that infestation with *Demodex folliculorum*, particularly in large number, could cause rosacea.

Seborrheic Dermatitis (SD)

SD is a common, chronic inflammatory dermatosis having a distinctive distribution in areas rich in sebaceous glands. The yeast *P. ovale*, various bacteria and, in infants, *Candida albicans* are found in increased numbers within the lesions, though it is not known whether their role is primary or secondary. Antifungal agents such as ketoconazole effectively control the disease, supporting the etiological role of *P. ovale*, although it is not clear as to how *P. ovale* causes inflammation and desquamation.

Anaerobic Infections of the Skin

Anaerobic bacteria are frequently found in infections of the sin, soft tissue, bones and in bacteremia. Injury to skin, bone or soft tissue by trauma, ischemia or surgery creates a suitable environment for anaerobic infections. Because the sites that are colonized by anaerobic bacteria contain many species of bacteria, disruption of anatomic barriers allows penetration of many organisms, resulting in mixed infections involving multiple species of anaerobes, combined with facultative or microaerophilic organisms.

Two-thirds of clinically significant anaerobic infections involve following five anaerobes: *Bacteroides fragilis* group, *Bacteroides melaninogenicus* group, *Fusobacterium nucleatum, Clostridium perfringens* and *anaerobic cocci*. Certain types of infections commonly involve anaerobic bacteria, including lower extremity infections in diabetics or in patients with severe peripheral vascular disease.

Leishmaniasis

Leishmaniasis is a parasitic infection caused by many species of the genus *Leishmania*, which belongs to the family Trypanosomatidae. The spectrum of disease ranges from a single innocuous cutaneous lesion to a fatal condition. Leishmaniasis can be either a zoonosis or an anthroponosis (transmitted from man to man). Transmission occurs through the bite of the infected sandfly, or as a congenital infection, through blood transfusion and possibly even by coitus. The incubation period varies from two weeks to one year.

The natural history of cutaneous Leishmaniasis is prolonged and has different clinical manifestations in different stages of its course. The typical lesion is usually located on areas exposed at night, namely the face and hands. The initial lesion is an erythematous papule, which resembles an insect bite and steadily enlarges over several weeks with varying degrees of ulceration and crustings. The fully developed lesion persists for several months and the resultant ulcer heals by scarring in about six months to two years. Though the lesion is usually solitary, numerous lesions occur in those who sustain multiple bites. The persistence of the lesion beyond a year usually indicates failure of natural healing and predicts chronicity and resistance to treatment. Leishmaniasis may turn to be relapsing chronic, disseminated, mucocutaneous, lymphatic, or even visceral, being lethal if untreated.

Local treatment is usually with antiparasitic agents or antibiotics (paramomycin, sodium stibogluconate, meglumine antimonite, rifampicine, metronidazole . . . ).

Scabies

Scabies is essentially a disease of children, and since the itch mite cannot survive for more than a few days away from the skin, the most significant factor in the transmission of scabies is prolonged intimate contact especially within the household. *Sarcoptes scabiei*, the causative agent of human scabies, belongs to the suborder Astigmata and family Sarcoptidae.

Once fertilized, the female can burrow into the skin. She burrows through the stratum corneum and granular layer up to the Malpighian level, and deposits 2 to 3 eggs per day; she can lay about 10-25 eggs and lives and dies in the burrow after about 30 days. Larvae emerge from the eggs after 3 to 4 days, wander to the skin surface and form shallow pockets in the original or a new host. The mite favors hands and wrists, but can also be present in elbows, feet, ankles, penis and scrotum. Itching undoubtedly is the predominant symptom, and worsens at night.

The burrow is the pathognomonic lesion of scabies, and its open end is marked by a minute papule or papulovesicle, which is the symptom most commonly observed. Animal transmitted scabies can be acquired from a variety of animals, dogs being the major source. Secondary pyoderma presenting as impetigo, ecthyma and furunculosis are the most common complications.

Antiscabetic medicines must be applied to the entire body, after a good scrub bath with soap and water, and after drying the skin. The patient should change his bedclothes, sheets, and pillow cover. All members of the personal household and other intimate contacts should be treated at the same time.

1% GBH lotions and creams are usually used in the treatment of scabies, as well as 25% benzyl benzoate emulsions, 10% crotamiton lotions and creams, and 0.5% liquid malathion.

Trichomoniasis

*Trichomonas vaginalis*, which invades the vagina, urethra, prostate and epididymis to cause *Trichomonas* is a pear-shaped, flagellate protozoon. Sexual intercourse is the major means of transmission of *Trichomonas vaginalis*; non-sexual transmission has an insignificant role. The prevalence of *Trichomonas vaginalis* ranges between 10 and 15% in healthy women. Trichomoniasis is usually asymptomatic in the male.

By females, it presents with pruritus of the vagina and vulva as the prominent feature. Dysuria may accompany infection, as well as dyspareunia and lower abdominal pain. Vaginal examination reveals a frothy, greenish-yellow discharge. Definitive diagnosis depends on the demonstration of the organism, either by direct microscopic examination of the vaginal discharge, or by culture. The treatment of choice is by oral metronidazole, completed by local intravaginal treatment with the same metronidazole.

Vaginitis with *Gardnerella*

*Gardnerella vaginalis* is a facultative anaerobic gram-variable rod. It has been demonstrated to cause a wide variety of infections; however it is most commonly recognized for its role as one of the organisms responsible for bacterial vaginosis (By). BV is the most common cause of vaginitis and the most common infection encountered in the outpatient gynecologic setting. An increase in vaginal discharge and vaginal malodor caused by a change in the vaginal flora characterizes BV. The vaginal discharge of BV characteristically is described as a thin, gray, homogenous fluid adherent to the vaginal mucosa.

Many studies have demonstrated the relationship of *G. vaginalis* with other bacteria in causing BV, known to be a synergistic polymicrobic infection. Some of the associated bacteria include *Lactobacillus* species and anaerobes, including *Mobiluncus, Bacteroides, Peptostreptococcus, Fusobacterium, Veillonella, Eubacterium, Mycoplasma hominis, Ureaplasma urealyticum* and *Streptococcus viridans*. In BV, the vaginal flora becomes altered: the lactobacilli population is reduced greatly, while populations of various anaerobes and *G. vaginalis* are increased.

Although BV is not considered as a sexually transmitted disease, sexual activity has been linked to the development of this infection. *G. vaginalis* has been reported to occur in up to 100% of women with signs and symptoms of BV, and the incidence of BY in patients attending obstetric clinics was told to be 10-25%. While uncomplicated BV typically resolves with standard antibiotic treatment, long-standing or untreated BV may lead to more serious sequelae, such as endometritis, salpingitis, pelvic inflammatory disease or complications of pregnancy. Clinical diagnosis of BV relies on history, vaginal examination and microscopic examination. Antibiotics are the mainstay of therapy for BV. Treatments include oral metronidazole and clindamycin and metronidazole vaginal gel.

Veterinary Infections: Canine Scabies

Canine scabies is a common transmissible skin disease affecting dogs and foxes. The parasites may induce severe allergic reactions. It is caused by infestation of the canine *Sarcoptes scabiei* mite. The microscopic mange mites burrow deep into the skin, laying eggs inside the burrows. The eggs hatch at larval state, the larval mites then move up to the skin surface and begin forming new burrows in the healthy sin tissue. Development from egg to adult is completed in approximately 2 weeks. The lesions resulting from infestations by these mites are a consequence of a reaction of the dog's immune system to the mites' presence.

Due to the intensity of the dog's immunological response, it takes only a small number of mites to produce widespread lesions and generalized dermatitis. Mange lesions often appear first around the tail, legs and feet. The first sign of infestation is usually hair loss due to the dog rubbing as it tries to relieve the itching. As infestation progresses, the lesions become severe and widespread representing a serious threat to welfare. Scabies occurs in dogs of all ages, and is spread around the world through contact with other dogs.

Sarcoptic mange mites are almost invisible to the naked eye. In addition, mange is only one of several conditions resulting in similar symptoms. Confirmation is traditionally by presence of the mite, eggs or faeces in skin scrapings and microscopic examination. However, because they are only present in small numbers in many cases they are not detected. Diagnosis of canine scabies by serological tests has been evaluated and the sensitivity and specificity of ELISA testing is very good.

Treatment begins usually by clipping the hair from the affected area, and then, an anti-seborrheic shampoo that breaks down and removes crusts, skin oil and debris is applied. Next, a parasiticidal dip is applied to the entire body, once a week for at least 4-6 weeks. Other treatments include the use of injectable or oral ivermectin, highly effective but with severe side effects, susceptible of causing death. The newest treatment for canine scabies is selamectin, a topical parasiticide effective in treating a number of different parasitic infestations in dogs and cats.

Veterinary Infection: Demodectic Mange

Demodectic mange (DM) also named red mange, or puppy mange, is a skin disease, generally of young dogs, caused by the mite *Demodex canis*. This mite lives, without causing any harm or irritation, on the bodies of virtually every adult dog and most human beings, inside the hair follicles, hence the name of follicular mange. Whether or not *Demodex* causes harm to a dog depends on the animal's ability to keep the mite under control.

Demodectic mange is not a disease of poorly kept or dirty dogs, but rather a disease of young dogs that have inadequate or poorly developed immune systems or older dogs that are suffering from a depressed immune system. The immune system normally keeps the number of mites in check and most dogs never develop disease from the mite. However if the immune system is weakened by disease or medications that are immune suppressive, the mites may multiply and cause disease. It is believed that susceptibility to mange can also be inherited. Since there is no easy test to determine immune status, it is impossible to predict which pets will get this disease, or how well a pet will heal if it shows symptoms of *Demodex*. Demodectic mange affects all breeds and occurs worldwide. This is the most common type of mange in dogs, after sarcoptic mange.

The life cycle of *Demodex canis* is not well known, but it appears to occur continuously within the hair follicles and sebaceous glands of the dog. The demodectic mite spends its entire cycle on the dog: eggs are laid by a pregnant female, hatch, and then mature from larvae to nymphs to adults. The mites are transferred directly from the mother to the puppies within the first week of life. Transmission of the mites is by direct contact only. That is, the mother and puppy must be physically touching, as the parasite cannot survive off the animal: kennel or bedding areas do not become contaminated and therefore the environment does not need to be treated. Lesions usually appear first around the puppy's head, as this is the area most in contact with the mother. Virtually every mother carries and transfers mites to her puppies, but most puppies are immune to the mite's effects and display no clinical signs or lesions. This infection is not contagious for humans nor other dogs, and isolation from non-affected dogs is not necessary.

Individuals sensitive to the mites may develop a few (less than five) lesions or they may have generalized mange, involving the entire body. The lesions and signs of Demodectic mange usually involve hair loss, crusty, red skin and at times a greasy or moist appearance. Usually, hair loss begins around the muzzle, eyes and other areas on the head. In localized mange, a few circular crusty areas will be noted, most frequently around the muzzle. Most of the lesions will self-heal as the puppies become older and develop their own immunity.

In cases of generalized mange, the skin is crusty and often inflamed; it will often crack and ooze a clear fluid. Some animals can become quite ill and develop fever, loss of appetite and become lethargic. Irritation from the follicle mites causes hair loss and thickened, wrinkled skin. Large abscesses usually develop in infested dogs from bacterial invasion of the enlarged follicles and itching may cause further damage.

Once Demodectic mange is suspected it can usually be confirmed by skin scraping or biopsy in which the mites can be seen with a microscope, as they are too small to be seen with the naked eye. A positive skin scraping of large numbers of *Demodex* mites, along with alopecia is the verification of *Demodex* mange. In such cases, treatment is necessary but *Demodex* is very difficult to eliminate; such treatment is usually accomplished with lotion dips and shampoos. Fortunately 90% of Demodectic mange cases are localized, in which only a few small areas are involved and can often be treated topically. 1% rotenone ointment and 5% benzoyl peroxide are commonly used in daily application.

If a dog develops generalized demodicosis, more aggressive treatment is usually required, the treatment of choice continuing to be AMITRAZ® dips applied every two weeks. Dips must continue until there have been no mites found on the skin scrapings taken after two successive treatments. In case of no response, additional treatment has to be instituted. Two new products recently appeared: ivermectin and milbemycin oxime, both of them showing efficacy but severe side effects. Unfortunately, euthanasia is the unique outcome for some dogs.

Quassinoids

Chemically, quassinoids are seco-triterpene-δ-lactones mostly found in the family Simaroubaceae (Vitanyi et al, 1997) and have been identified as the major class of compounds responsible for biological activity in this family (Dou, 1996). Quassinoids are biosynthetically related to triterpenes and share the same metabolic precursors; they are secondary metabolites with phytotoxic and allelopathic activities (Dayan et al, 1999). So far, 170 quassinoids have been isolated and characterized.

As deduced from structure-activity relationship analysis most potent quassinoids have a pentacyclic ring system with a lactone function and a methylene-oxygen ring bridge linking C-8 and C-13 (e.g. brusatol) or C-11 (e.g. ailanthinone) (Samuelson, 1992). Following are a certain number of quassinoids isolated and characterized at this time (Tirimana, 1987; Duke, 1992):

| | |
|---|---|
| Brusatol | Ailanthinon |
| Simalikalactone D | Quassin |
| 15-desacaetylundulatone | Chaparrinone |
| 15β-heptylchaparrinone | Neoquassin |
| Isoquassin | Parain |
| Quassimarin | Quassinol |
| Quassol | 18-hydroxy-quassin |
| Ailantinol A | Ailantinol B |
| Ailantinol C | Ailantinol D |
| Ailantinol E | Ailantinol F |
| Ailantinol G | Bruceanol A |
| Bruceanol B | Bruceanol C |
| Bruceanol D | Bruceanol E |
| Bruceanol F | Bruceanol G |
| Bruceanol H | Picrasinol A |
| Picrasinol B | Picrasinol C |
| Picrasinol D | Bruceoside A |
| Bruceoside B | Bruceoside C |
| Picrasinoside A | Picrasinoside B |
| Picrasinoside C | Picrasinoside D |
| Picrasinoside E | Picrasinoside F |
| Picrasinoside G | Picrasinoside H |
| Eurycomanone | 2-acetylglaucarubine |
| 13,18-dehydroglaucarubine | Glaucarubinone |
| Glaucarubine | Holacanthone |
| 20-simarolide | Simarubolide |
| Dehydroquassin | Isoparain |
| Nigakilactone A | Norneoquassin |
| Quassialactol | |

These compounds are given solely as examples of quassinoids for the purpose of illustration and not construed as limitations of the present invention as many variations thereof are possible without departing from the spirit and scope.

It was known by prior investigations and literature, that quassinoids had a wide spectrum of biological activity, among them anti-leukemic, anti-tumorous, antimalarial, amoebicidal, anti-ulcerogenic and nociceptive ones.

From earlier time, vegetal extracts containing quassinoids are used as a natural insecticide, and appeared to be an effective treatment for lice infestations in humans. *Quassia* wood is on the FDA's GRAS (Genus Regarded As Safe) list.

Sources of Quassinoids

Most of quassinoids are sourced from plants of the family Simaroubaceae, a pantropical family consisting of six subfamilies with 32 genera and more than 170 arborescent and shrubby species (Simao et al, 1991; Fernanda and Quinn, 1995). Species in the genus *Quassia* are the best known in traditional medicine in Latin America. Most used are *Quassia indica, Quassia cedron, Quassia amara, Quassia alatifolia, Quassia officinalis, Quassia amargo*. Other species of medicinal significance are *Picramnia pentadra, Picrasma excelsa, Simarouba versicolor, Simarouba amara, Simarouba glauca, Simarouba officinalis, Ailanthus altissima* and *Eurycema longifolia*, although this listing is not exhaustive and given solely as examples for the purpose of illustration and not construed as limitations of the present invention as many variations thereof are possible without departing from the spirit and scope.

DESCRIPTION OF THE INVENTION

The present invention relates to pharmaceutical or derma-cosmetic formulations for topical and intravaginal application suitable for the treatment of various topical and vaginal infections, as well in humans as in veterinary medicine. More particularly, the present compositions comprise of one or more quassinoids, or plant extracts containing these phytochemicals.

Now, the inventors of the present invention have been able to observe that quassinoids, as well as plant extracts containing those active ingredients, are particularly active on *Demodex folliculorum* and *Demodex canis*, more precisely they are able to eradicate this parasite with a very strong effect. Furthermore, the same parasiticide activity has been observed on *Sarcoptes scabiei*, but also on *Leishmania* and *Trichomonas vaginalis*. Moreover, the inventors have been able to observe that these active ingredients, and vegetal extracts containing them, show a strong bactericidal activity on most of anaerobic rods, especially *Gardnerella vaginalis*.

The first object of the invention is the use of compositions comprising quassinoids in the above cited therapeutical indications in human or in veterinary medicine. More particularly the invention is the use of a composition comprising quassinoids in the treatment of vaginitis, and this use wherein vaginitis is vaginitis with Gardenerella.

It is also the use of a composition comprising quassinoids in the treatment of Trichomoniasis.

It is also the use of a composition comprising quassinoids in the treatment of parasitic infections of the skin or mucosa, and this use wherein the parasitic infections is caused by Leishmaniaisis Trypanosomatidae.

It is also the use of a composition comprising quassinoids in the treatment of anaerobic infections of the skin, and this use wherein the anaerobic infections involve at least one of the following five anaerobes, *Bacteroides fragilis* group, *Bacteroides malaninogenicus* group, *Fusobacterium nucleatum, Clostridium perfringens*, and *anaerobic cocci*.

It is also the use of a composition comprising quassinoids in the treatment of facial erythrosis, couperose or rosacea.

It is also the use of a composition comprising quassinoids in the treatment of cutaneous disorders caused by *Demodex folliculorum*.

It is also the use of a composition comprising quassinoids in the treatment of veterinary skin disease, and more particularly canine scabies, caused by infestations of the canine *Sarcoptes scabei* mite or the *Demodex canis* mite.

The present invention solves these technical problems for the first time in a satisfactory manner which can be used on the industrial scale for the preparation of dermo-cosmetic, dermatological, gynecological or veterinary compositions.

Thus, according to a first feature, the present invention relates to the use of one quassinoid, or a combination of two or more quassinoids, or a vegetal extract containing one or more quassinoids, or a combination of two or more vegetal extracts containing one or more quassinoids, for the manufacture of a dermo-cosmetic or pharmaceutical composition, especially dermatological, or gynecological, or veterinary composition.

According to one particular characteristic, the above mentioned quassinoid (s), or combination of two or more quassinoids, is (are) chosen among the following substances: Brusatol, Ailanthinon, Simalikalactone D, Quassin, 15-desacaetylundulatone, Chaparrinone, 15β-heptylchaparrinone, Neoquassin, Isoquassin, Parain, Quassimarin, Quassinol, Quassol, 18-hydroxy-quassin, Ailantinol A, Ailantinol B, Ailantinol C, Ailantinol D, Ailantinol E, Ailantinol F, Ailantinol G, Bruceanol A, Bruceanol B, Bruceanol C, Bruceanol D, Bruceanol E, Bruceanol F, Bruceanol G, Bruceanol H, Picrasinol A, Picrasinol B, Picrasinol C, Picrasinol D, Bruceoside A, Bruceoside B, Bruceoside C, Picrasinoside A, Picrasinoside B, Picrasinoside C, Picrasinoside D, Picrasinoside E, Picrasinoside F, Picrasinoside G, Picrasinoside H, Eurycomanone, 2-acetyiglaucarubine, 13,18-dehydroglaucarubine, Glaucarubinone, Glaucarubine, Holacanthone, 20-simarolide, Simarubolide, Dehydroquassin, Isoparain, Nigakilactone A, Norneoquassin, Quassialactol.

According to another particular characteristic, the vegetal extract containing one or more quassinoids is obtained from plants of the family Simaroubaceae, especially genus *Quassia, Picramnia, Picrasma, Simarouba, Ailanthus* and *Eurycema*, especially from the barks of trunks, stalks or roots of these plants.

According to another particular characteristic, the above mentioned extract is an extract obtained by extraction with at least one polar solvent such as water, an alcohol, preferably a lower alcohol such as methanol or ethanol, a glycol, in particular propylene glycol, or an aqueous-alcoholic mixture in any proportions.

According to another particular characteristic, the above mentioned quassinoid (s) is (are) present in the composition at a concentration of between 0.001 µg/ml to 0.1 µg/ml, while the above mentioned extract is present in the composition at a concentration of between 0.001 and 5% by weight, preferably of between 0.005 and 1% and particularly of between 0.01 and 0.15% by weight, expressed as dry extract and based on the total weight of the composition.

According to another particular characteristic, the above mentioned composition can also contain an active agent selected from the group consisting of esculin, escin, a ficaria extract, a chestnut extract, a mimosa tenuiflora extract, allantoin, 18β-glycyrrhetinic acid, α-bisabolol, metronidazole.

According to yet another particular characteristic, the above mentioned composition can also contain an active agent selected from the group consisting of gamma-benzene hexachloride (GBH), benzoyl benzoate, crotamiton, malathion, permethrin, lindane, 18β-glycyrrhetinic acid, lidocaine, prilocalne, articaine, bupivacaine, mepivacaine, procaine, ropivacaine, pramocaine.

According to yet another particular characteristic, the above mentioned composition can also contain an active agent selected from the group consisting of mepacrine, sodium stibogluconate, meglumine antimonate, paramomycin, methyl benzethonium, chlorpromazine, ketoconazole, itraconazole, rifampicin, dapsone, metronidazole, levamisole, chloroquine, nifurtimox, amphotericin B, potassium iodide.

According to yet another particular characteristic, the above mentioned composition can also contain an active agent selected from the group consisting of cetrimide, tar, salicylic acid, resorcinol, zinc pyrithione, selenium sulphide, corticoids, iodohydroxyquinolone, chlorhexidine, ketoconazole, urea.

According to yet another particular characteristic, the above mentioned composition can also contain an active agent selected from the group consisting of clindamycin or metronidazole.

According to yet another particular characteristic, the above mentioned composition can also contain an active agent selected from the group consisting of metronidazole, ornidazole, secnidazole, tenonitrozole, tinidazole.

According to yet another particular characteristic, the above-mentioned composition can also contain an active agent selected from the group consisting of rotenone, benzoyl peroxide, amitraz, ivermectin, milbemycin oxime.

Other particular characteristics of the dermo-cosmetic or pharmaceutical composition, especially dermatological, gynecological and veterinary composition, are clearly apparent from the foregoing description relating to the various particular characteristics of the use, and are also apparent to those skilled in the art from the complete description of the invention, which is illustrated especially by the Examples below.

An above described composition according to the invention, containing one or more quassinoids, or one or more vegetal extracts containing one or more quassinoids, can be presented in different forms usable in derma-cosmetics or dermatology, such as gels, creams, ointments, lotions, milks, powders, foams, or in forms compatible with gynecological practice: gynecological tablets or capsules, vaginal suppositories, gels, creams, lotions, milks, powders or foams.

In this context, the quassinoid (s) or the vegetal extract (s) containing quassinoid (s) is usually incorporated into a dermo-cosmetically or dermatologically acceptable excipient.

Also, within the framework of the invention, if the composition is a derma-cosmetic composition, the above-mentioned quassinoid (s) or the vegetal extract containing quassinoid(s) can advantageously be incorporated into a dermo-cosmetically acceptable excipient.

Likewise, if this composition is a pharmaceutical composition, the above-mentioned quassinoid (s) or the extract containing quassinoid (s) can be incorporated into a pharmaceutically acceptable excipient, especially a dermatologically acceptable excipient or an excipient suitable to gynecological uses or veterinary practice.

Such excipients are well known to those skilled in the art and also follow from the description of several composition examples below.

Thus, other objects, characteristics and advantages of the invention will become clearly apparent from the following explanatory description referring to several illustrative examples of the invention, which cannot therefore in any way limit the scope of the invention. In the present description, including the examples, the percentages are given by weight unless indicated otherwise.

Example 1

Aqueous Extract of *Quassia* Root

An extract of root of the shrub *Quassia amara*, originating from Argentina, is subjected to a Soxhlet-type extraction with water, i.e. under reflux for several hours. The solvent/root ratio is generally 10/1 by weight.

After extraction, this extract is generally concentrated for derma-cosmetic or pharmaceutical use.

Of course, as it can easily be understood by those skilled in the art, the removal of the solvent, in this case water, can be continued by evaporation under reduced pressure or by lyophilization, until a dry extract is obtained.

Example 2

Methanolic Extract of *Picrasma Excelsa* Wood 100 grams of wood of the tree *Picrasma excelsa*, originating from Jamaica, are extracted with 1 liter of methanol by the Soxhlet method for several hours under reflux.

After extraction, the methanolic extract is concentrated under a product containing very little methanol.

Example 3

Hydroglycolic Extract of *Quassia* Bark

An extract of the bark of the small tree *Quassia amara*, originating from Argentina, is subjected to a Soxhlet-type extraction with propylene glycol/water (50:50), i.e. under reflux for several hours. The solvent/bark ratio is generally 10/1 by weight.

After extraction, the extract is generally concentrated for dermo-cosmetic or pharmaceutical use.

Example 4

Ethanolic Extract of *Simarouba* Root Bark 100 grams of root bark of the tree *Simarouba amara*, originating from Guiana, are extracted with 1-liter ethanol by the Soxhlet method for several hours under reflux.

After extraction, the ethanolic extract is concentrated until a product containing very little ethanol is obtained.

Example 5

Demonstration of the Acaricide Activity of the Extracts on *Demodex Folliculorum*

12 patients with papulopustular rosacea were studied. Prevalence and density of *Demodex folliculorum* were estimated by microscopic examination of the expressed follicular content. *Demodex folliculorum* was detected in 11 (91.7%) of the 12 rosacea patients. The mean mite density was 2.08 mites/visual field.

Once the sample of the expressed follicular content was under microscope examination, and the presence of *Demodex folliculorum* detected, the microscopic observation was focused on one of these parasites, in order to verify that it was still alive, through its movements. Then, one droplet of the extract under example 3 was laid at the junction between the microscope slide and lamellae, thanks to a pipette.

Thus, the extract was able to get immediately in touch with the *Demodex folliculorum* under observation, and in all 11 cases of patients with presence of *Demodex folliculorum*, it was possible to observe the sudden death of the parasite, by absence of further movements, and apparent lysis of its body structure. Thus, the extracts appeared to have a considerable miticide activity on *Demodex folliculorum*.

Example 6

Demonstration of the Antiscabetic Activity of the Extracts on *Sarcoptes Scabiei*

APLIGRAF®, a human skin equivalent, was used as a model to investigate the antiscabetic activity of the extracts on *Sarcoptes scabiei*.

APLIGRAF® is a living, bi-layered skin substitute: the epidermal layer is formed by human keratinocytes and has a well-differentiated stratum corneum; the dermal layer is composed of human fibroblasts in a bovine Type 1 collagen lattice. While matrix proteins and cytokines found in human skin are present in APLIGRAF®, the latter does not contain Langerhans cells, melanocytes, macrophages, lymphocytes, blood vessels nor hair follicles. *Sarcoptes scabiei* mites were collected in outpatients of a dermatology department, by skin scrapings.

The mites collected were immediately placed on the surface of APLIGRAF®, and burrowed very quickly into the stratum corneum, the burrows being visible with naked eye and yet more with a loupe, and very characteristic.

In order to assess the antiscabetic activity of the extracts on *Sarcoptes scabiei*, one drop of such extracts was placed on the external orifice of the burrows, and an overnight scraping was realized on the human skin equivalent, in order to collect the mites, and place them in mineral oil on a slide, then placing a glass coverslip on top, and reading at 10× objective.

In all cases, investigators were able to observe debris of mites, or dead mites, but never alive mites, showing the rapid and efficient antiscabetic activity of the extracts on *Sarcoptes scabiei*. These results were observed with all the extracts presented as Examples 1 to 4.

Example 7

Demonstration of the Anti-Protozoal Activity of the Extracts on *Trichomonas Vaginalis*

*Trichomonas vaginalis*, which invades the vagina, urethra, prostate and epididymis to cause Trichomoniasis is a pear-shaped, flagellate protozoon measuring 10 μm in length and 7 μm in width, thus visible by microscopic examination.

Direct microscopic examination of the vaginal discharge is a rapid and reliable method for diagnosis: a small amount is mixed on a glass slide with a drop of saline, a coverslip is applied and the preparation is scanned under a microscope. *Trichomonas* are characteristic by their pear shape, as well as by the presence of a motile flagellum.

*Trichomonas* may be cultured using a variety of liquid or semi-solid media, including the Fienberg-Whittington medium. Cultures may become positive within 48 hours. They will detect a small number of organisms, but, because the doubling time is long (8-12 hours) they must be observed for 10-12 days before they can be reliably regarded as negative.

In order to demonstrate the anti-protozoal activity of the extracts on *Trichomonas vaginalis*, patients from outpatient gynecological setting were put under investigation in search of the presence of *Trichomonas vaginalis* in their vaginal discharge by direct microscopic examination.

Those patients found to be positive by direct microscopic examination (8 of 50 patients, i.e. 16%) were sampled and the samples of vaginal discharge were cultured in Fienberg-Whittington medium. After 5 days, all cultures (i.e. 8 media) were found to be positive. On the 6$^{th}$ day, small disks impregnated with the extracts of the examples 1 to 4 were laid on these 8 cultures, and observed after 48 hours. In all 8 cultures, all four extracts demonstrated to have an anti-protozoal activity on *Trichomonas vaginalis*, although it being unequal (ex.3>ex.1>ex.2>ex.4).

Various examples of dermo-cosmetic or pharmaceutical compositions according to the invention, especially dermatological compositions, compositions featured for gynecological use and formulations aimed to veterinary practice according to the invention, using one or more quassinoids, or one or more vegetal extracts containing one or more quassinoids, are given below.

Example 8

Dermo-Cosmetic or Dermatological Composition for the Treatment of Facial Erythrosis, Couperose or Rosacea, in the Form of a Gel

| | |
|---|---|
| Hydroglycolic extract of *Quassia amara* of example 3 | 0.5 g |
| Carbopol Ultrez 10 | 0.5 g |
| Pemulen TR2 | 0.25 g |
| Germaben II | 1.00 g |
| Sodium hydroxide | qsp pH 5.5 |
| Water | qsp 100 g |

This gel is applied locally twice a day for at least 6 weeks to the zones of skin to be improved.

Example 9

Dermo-Cosmetic or Dermatological Composition for the Treatment of Facial Erythrosis, Couperose or Rosacea in the Form of a Cream

| | |
|---|---|
| Methanolic extract of *Picrasma excelsa* of example 2 | 1 g |
| *Mimosa tenuiflora* extract | 2 g |
| *Ficaria ranunculoides* extract | 1 g |
| Esculin | 1 g |
| Cetyl alcohol (and) Ceteth-20 (and) Steareth-20 | 12 g |
| Paraffin oil | 2 g |
| Alpha-bisabolol | 0.2 g |
| 18β-glycyrrhetinic acid | 0.2 g |
| Germaben II | 1 g |
| Water | qsp 100 g |

This cream is applied topically twice a day for at least 6 weeks to the areas of the skin affected.

Example 10

Milk for the Treatment of Facial Erythrosis, Couperose or Rosacea

| | |
|---|---|
| Aqueous extract of *Quassia amara* of example 1 | 3 g |
| Hydroglycolic extract of *Aesculus hippocastaneum* | 2 g |
| Alpha-bisabolol | 0.2 g |
| 18β-glycyrrhetinic acid | 0.2 g |
| Glycerol | 2 g |
| Carbopol | 0.5 g |
| Glyceryl stearate | 2 g |
| PEG-30 glyceryl stearate | 3 g |
| Germaben II | 1 g |
| Water | qsp 100 g |

This milk is applied locally twice a day for at least 8 weeks on the face.

Example 11

Dermo-Cosmetic or Dermatological Preparation for the Treatment of Seborrheic Dermatitis Under the Form of a Gel

| | |
|---|---|
| Ethanolic extract of *Simarouba* root bark of example 4 | 0.5 g |
| Carbomer | 1 g |
| Triethanolamine | 0.3 g |
| Germaben II | 1 g |
| Water | qsp 100 g |

This gel is applied topically twice a day on a 2-3 week period to the affected area.

Example 12

Dermo-Cosmetic or Dermatological Preparation for the Treatment of Seborrheic Dermatitis Under the Form of a Cream

| | |
|---|---|
| Hydroglycolic extract of *Quassia amara* of example 3 | 0.4 g |
| Zinc pyrithione | 1.5 g |
| Cetyl alcohol (and) Ceteth-20 (and) Steareth-20 | 8 g |
| Paraffin oil | 3 g |
| Stearic acid | 1 g |
| Kathon CG | 0.1 g |
| Water | qsp 100 g |

This cream is applied twice a day on a 2-3 week period to the area affected by seborrheic dermatitis.

Example 13

Dermatological Cream for the Treatment of Seborrheic Dermatitis

| | |
|---|---|
| Methanolic extract of *Picrasma excelsa* of example 2 | 0.2 g |
| Salicylic acid | 2 g |
| Betamethasone | 0.05 g |
| Glycerol | 3 g |
| Paraffin | 3 g |
| Cetearyl alcohol | 5 g |
| Sodium cetearyl sulfate | 4 g |
| Stearic acid | 0.4 g |
| Sodium sulfate | 0.1 g |
| Germaben II | 1 g |
| Water | qsp 100 g |

This cream is used once a day on 2-week periods on the lesions.

Example 14

Dermatological Milk for the Treatment of Seborrheic Dermatitis

| | |
|---|---|
| Aqueous extract of *Quassia amara* of example 1 | 2 g |
| Selenium sulphide | 2.5 g |
| Desonide | 0.1 g |
| Cetearyl ethylhexanoate | 6 g |
| Cetearyl alcohol (and) cetearyl glucoside | 1 g |
| Ceteth-20 | 1 g |
| Polyacrylamide | 1.5 g |
| Germaben II | 1 g |
| Water | qsp 100 g |

This milk is used once a day on 2-week periods on the lesions of seborrheic dermatitis.

Example 15

Dermatological Shampoo for the Treatment of Seborrheic Dermatitis

| | |
|---|---|
| Aqueous extract of *Quassia amara* of example 1 | 0.5 g |
| Selenium sulphide | 2 g |
| Salicylic acid | 2.5 g |
| Disodium Cocoamphodiacetate | 6 g |
| Sodium lauryl ether sulfate | 18 g |
| Tween 20 | 6 g |
| Glutamate DOE 120 | 4 g |
| Glucam E20 | 1 g |
| Water | qsp 100 g |

This shampoo is used 2-3 times a week for hygienic care of seborrheic scalps.

Example 16

Dermatological Gel for the Treatment of Cutaneous Leishmaniasis

| | |
|---|---|
| Hydroglycolic extract of *Quassia amara* of example 3 | 5 g |
| Cetearyl octanoate | 25 g |
| Glycerin | 4 g |
| Polyacrylamide | 1 g |
| Germaben II | 1 g |
| Water | qsp 100 g |

This gel has to be applied once a day on the lesions, on large periods of time.

Example 17

Dermatological Ointment for the Treatment of Cutaneous Leishmaniasis

| | |
|---|---|
| Ethanolic extract of *Simarouba amara* of example 4 | 0.5 g |
| Paramomycin | 15 g |
| Lanolin/Paraffin (50:50) | 84.5 g |

This ointment is used once a day on the lesions, on large periods of time.

Example 18

Dermatological Cream for the Treatment of Human Scabies

| | |
|---|---|
| Hydroglycolic extract of *Quassia amara* of example 3 | 0.5 g |
| Pramocaine | 1 g |
| Cetyl alcohol (and) Ceteth-20 (and) Steareth-20 | 8 g |
| Paraffin oil | 3 g |
| Stearic acid | 1 g |
| Kathon CG | 0.1 g |
| Water | qsp 100 g |

This cream is applied topically once a day on a 2-3 week period on the scabies lesions.

Example 19

Dermatological Lotion for the Treatment of Human Scabies

| | |
|---|---|
| Ethanolic extract of *Simarouba amara* of example 4 | 0.5 g |
| Crotamiton | 10 g |
| Ethanol 96° | qsp 100 g |

This lotion is applied locally on the lesions of the skin once a day during 10-20 days.

Example 20

Dermatological Milk for the Treatment of Human Scabies

| | |
|---|---|
| Methanolic extract of *Picrasma excelsa* of example 2 | 0.2 g |
| Permethrin | 5 g |
| 18β-glycyrrhetinic acid | 1 g |
| Cetearyl ethylhexanoate | 6 g |
| Cetearyl alcohol (and) cetearyl glucoside | 1 g |
| Ceteth-20 | 1 g |
| Polyacrylamide | 1.5 g |
| Germaben II | 1 g |
| Water | qsp 100 g |

This milk is applied locally to the lesions once a day during a 2-3 week period.

Example 21

Vaginal Suppositories for the Treatment of Trichomoniasis or Vaginitis with *Gardnerella Vaginalis*

| | |
|---|---|
| Methanolic extract of *Picrasma excelsa* of example 2 | 0.2 g |
| Semi-synthetic glycerides | 99.8 g |

In this example, the semi-synthetic glycerides used were WITEPSOL S55 and WITEPSOL E85 marketed by Farma International, PO Box 141654, Coral Gables, Fla., USA. The vaginal suppositories are used once a day, preferably at night, during one week.

Example 22

Vaginal Suppositories for the Treatment of Trichomoniasis or Vaginitis with *Gardnerella Vaginalis*

| | |
|---|---|
| Hydroglycolic extract of *Quassia amara* of example 3 | 0.5 g |
| Semi-synthetic glycerides | 99.5 g |

In this example, the semi-synthetic glycerides used were SUPPOCIRE Standard Type marketed by Gattefossé SA, 36 Chemin de Genas, F-69800 France. The vaginal suppositories are used once a day, preferably at night, during one week.

Example 23

Vaginal Suppositories for the Treatment of Trichomoniasis or Vaginitis with *Gardnerella Vaginalis*

| | |
|---|---|
| Aqueous extract of *Quassia amara* of example 1 | 2.5 g |
| Gelatin | 0.5 g |

The vaginal suppositories are used once a day, preferably at night, during one week.

Example 24

Vaginal Capsules for the Treatment of Trichomoniasis or Vaginitis with *Gardnerella Vaginalis*

| | |
|---|---|
| Methanolic extract of *Picrasma excelsa* of example 2 | 25 mg |
| Lactose | 275 mg |

In a gelatin capsule n° 0

The vaginal capsules are used once a day, preferably at night, during one week.

Example 25

Intravaginal Cream for the Treatment of Trichomoniasis or Vaginitis with *Gardnerella Vaginalis*

| | |
|---|---|
| Ethanolic extract of *Simarouba amara* of example 4 | 0.5 g |
| Cetearyl octanoate | 25 g |
| Glycerin | 4 g |
| Polyacrylamide | 3 g |
| Germaben II | 1 g |
| Water | qsp 100 g |

The cream is applied intravaginally and on the vulva once a day, preferably at night, during one week.

Example 26

Intravaginal Gel for the Treatment of Trichomoniasis or Vaginitis with *Gardnerella Vaginalis*

| | |
|---|---|
| Aqueous extract of *Quassia amara* of example 1 | 0.5 g |
| Carbopol Ultrez 10 | 0.5 g |
| Pemulen TR2 | 0.25 g |
| Germaben II | 1 g |
| Sodium hydroxide | qsp pH 5.5 |
| Water | qsp 100 g |

This gel is applied intravaginally and on the vulva once a day, preferably at night, during one week.

Example 27

Intravaginal Gel for the Treatment of Trichomoniasis or Vaginitis with *Gardnerella Vaginalis*

| | |
|---|---|
| Hydroglycolic extract of *Quassia amara* of example 3 | 0.5 g |
| Carbomer | 1 g |
| Triethanolamine | 0.5 g |
| Germaben II | 1 g |
| Water | qsp 100 g |

This gel is applied intravaginally and on the vulva once a day, preferably at night, during one week.

Example 28

Intravaginal Foaming Lotion for Prophylaxis and Treatment of Trichomoniasis and Vaginitis with *Gardnerella Vaginalis*

| | |
|---|---|
| Ethanolic extract of *Simarouba amara* of example 4 | 0.2 g |
| Sodium Laureth sulfate | 5 g |
| PEG-7 Glyceryl cocoate | 5 g |
| PEG-40 Hydrogenated Castor Oil | 4 g |
| Propylene glycol | 3 g |
| Cocamidopropylbetaine | 2 g |
| Kathon CG | 0.1 g |
| Water | qsp 100 g |

The lotion is used with water for intravaginal and external washing twice a day.

Example 29

Veterinary Lotion for the Treatment of Canine Scabies and Demodectic Mange

| | |
|---|---|
| Hydroglycolic extract of *Quassia amara* of example 3 | 0.5 g |
| POE Castor Oil | 2 g |
| Diethylenglycol monoethylether | 1.5 g |
| Methyl Paraben | 0.2 g |
| Water | qsp 100 g |

This lotion is commonly used on clipped-haired skin daily, during 3-6 weeks.

Example 30

Veterinary Foaming Lotion for the Treatment of Canine Scabies and Demodectic Mange

| | |
|---|---|
| Methanolic extract of *Picrasma amara* of example 2 | 0.2 g |
| Sodium Laureth Sulfate | 2 g |
| Salicylic acid | 0.2 g |
| Methyl Paraben | 0.2 g |
| Water | qsp 100 g |

This lotion must be applied daily during 3-6 weeks.

Example 31

Veterinary Shampoo for the Treatment of Canine Scabies and Demodectic Mange

| | |
|---|---|
| Ethanolic extract of *Simarouba amara* of example 4 | 0.3 g |
| Disodium cocoamphodiacetate | 6 g |
| Sodium lauryl ether sulfate | 15 g |
| Kathon CG | 0.1 g |
| Water | qsp 100 g |

This shampoo is currently used for washing the hair before applying a treating lotion.

Example 32

Veterinary Shampoo for the Treatment of Canine Scabies and Demodectic Mange

| | |
|---|---|
| Aqueous extract of *Quassia amara* of example 1 | 0.5 g |
| Sodium lauryl ether sulfate | 18 g |
| POE Castor Oil | 2 g |
| 18β-glycyrrhetinic acid | 0.5 g |
| Methyl Paraben | 0.2 g |
| Water | qsp 100 g |

This shampoo is currently used for washing the hair before applying a treating lotion.

Example 33

Veterinary External Powder for the Treatment of Canine Scabies and Demodectic Mange

| | |
|---|---|
| Hydroglycolic extract of *Quassia amara* of example 3 | 0.2 g |
| Talc | 49.4 g |
| Kaolin | 49.4 g |
| Magnesium stearate | 1 g |

Example 34

Veterinary Topical Gel for the Treatment of Canine Scabies and Demodectic Mange

| | |
|---|---|
| Methanolic extract of *Picrasma excelsa* of example 2 | 0.1 g |
| Carbomer | 1 g |
| Triethanolamine | 0.5 g |
| Methyl Paraben | 0.2 g |
| Water | qsp 100 g |

The gel is applied topically on clipped-haired skin once daily during 3-6 weeks.

What is claimed is:

1. A method for treating a condition caused by a parasitic or anaerobic bacterial infection of skin or mucosa, the method comprising:
    administering to a skin or mucus infected by a parasite or an anaerobic bacteria of a human or an animal a therapeutically effective amount of a composition consisting essentially of:
    a. an active agent consisting essentially of at least one quassinoid selected from the group consisting of Brusatol, Ailanthinon, Simalikalactone D, Quassin, Chaparrinone, 15-desacaetylundulatone, 15β-heptylchaparrinone, Neoquassin, Isoquassin, Parain, Quassimarin, Quassinol, Quassol, 18-hydroxy-quassin, Ailantinol A, Ailantinol B, Ailantinol C, Ailantinol D, Ailantinol E, Ailantinol F, Ailantinol G, Bruceanol A, Bruceanol B, Bruceanol C, Bruceanol D, Bruceanol E, Bruceanol F, Bruceanol G, Bruceanol H, Picrasinol A, Picrasinol B, Picrasinol C, Picrasinol D, Bruceoside A, Bruceoside B, Bruceoside C, Picrasinoside A, Picrasinoside B, Picrasinoside C, Picrasinoside D, Picrasinoside E, Picrasinoside F, Picrasinoside G, Picrasinoside H, Eurycomanone, 2-acetylglaucarubine, 13,18-dehydroglaucarubine, Glaucarubinone, Glaucarubine, Holacanthone, 20-simarolide, Simarubolide, Dehydroquassin, Isoparain, Nigakilactone A, Norneoquassin, and Quassialactol; and
    b. an optional dermo-cosmetically or pharmaceutically topically acceptable excipient wherein the parasite is selected from the group consisting of *Leishmaniaisis Trypanosomatidae, Demodex folliculorum, Sarcoptes scabei* and *Demodex canis*; and
    wherein the anaerobic bacteria is selected from the group consisting of *Bacteroides fragilis, Bacteroides malaninogenicus, Fusobacterium nucleatum, Clostridium perfringens*, and *Anaerobic cocci*.

2. The method of claim 1, wherein the infection is a parasitic infection.

3. The method of claim 2, wherein the parasitic infection is caused by Leishmaniaisis Trypanosomatidae.

4. The method of claim 1, wherein the infection is an anaerobic bacterial infection.

5. The method of claim 1, wherein the condition is facial erythrosis, couperose, rosacea, or seborrheic dermatitis.

6. The method of claim 1, wherein the condition is a cutaneous disorder caused by *Demodex folliculorum*.

7. The method of claim 1, wherein the condition is canine scabies caused by an infestation of canine *Sarcoptes scabei* mite or *Demodex canis* mite.

8. The method of claim 1, wherein the composition has a total concentration of quassinoid of between 0.001 μg/ml to 0.1 μg/ml in a dermo-cosmetically or pharmaceutically topically acceptable excipient.

* * * * *